(12) United States Patent
Andrianov et al.

(10) Patent No.: US 9,687,546 B2
(45) Date of Patent: Jun. 27, 2017

(54) IMMUNOSTIMULATING POLYPHOSPHAZENE COMPOUNDS

(71) Applicants: Alexander Andrianov, Belmont, MA (US); Alexander Marin, Newton, MA (US)

(72) Inventors: Alexander Andrianov, Belmont, MA (US); Alexander Marin, Newton, MA (US)

(73) Assignee: Innovo Biopolymers, LLC, Rockville, MD (US)

( * ) Notice: Subject to any disclaimer, the term of this patent is extended or adjusted under 35 U.S.C. 154(b) by 0 days.

(21) Appl. No.: 14/977,848

(22) Filed: Dec. 22, 2015

(65) Prior Publication Data

US 2016/0106833 A1    Apr. 21, 2016

Related U.S. Application Data

(63) Continuation of application No. 14/710,798, filed on May 13, 2015, now abandoned, which is a continuation of application No. 14/323,083, filed on Jul. 3, 2014, now abandoned, which is a continuation of application No. 13/743,824, filed on Jan. 17, 2013, now abandoned, which is a continuation of application No. 12/806,941, filed on Aug. 24, 2010, now abandoned, which is a continuation of application No. 11/355,737, filed on Feb. 16, 2006, now abandoned.

(60) Provisional application No. 60/654,567, filed on Feb. 18, 2005.

(51) Int. Cl.
| | | |
|---|---|---|
| A61K 8/72 | (2006.01) | |
| A61K 39/39 | (2006.01) | |
| A61K 31/80 | (2006.01) | |
| A61K 39/00 | (2006.01) | |
| C08G 79/025 | (2016.01) | |
| A61K 39/29 | (2006.01) | |
| C12N 7/00 | (2006.01) | |
| A61K 39/35 | (2006.01) | |
| A61K 31/74 | (2006.01) | |

(52) U.S. Cl.
CPC ............. *A61K 39/39* (2013.01); *A61K 31/80* (2013.01); *A61K 39/00* (2013.01); *A61K 39/292* (2013.01); *C08G 79/025* (2013.01); *C12N 7/00* (2013.01); *A61K 31/74* (2013.01); *A61K 39/35* (2013.01); *A61K 2039/55511* (2013.01); *A61K 2039/55555* (2013.01); *C12N 2730/10134* (2013.01)

(58) Field of Classification Search
None
See application file for complete search history.

*Primary Examiner* — James Rogers
(74) *Attorney, Agent, or Firm* — Raymond J. Lillie (57) ABSTRACT

Polyphosphazene polymers having immunomodulating activity, and the biomedical use of such polyphosphazene polymers, in conjunction with an antigen or an immunogen are disclosed.

1 Claim, 2 Drawing Sheets

IMMUNOSTIMULATING POLYPHOSPHAZENE COMPOUNDS

CROSS-REFERENCE TO RELATED APPLICATIONS

This Application is a continuation of application Ser. No. 14/710,798, filed May 13, 2015, which is a continuation of application Ser. No. 14/323,083, filed Jul. 3, 2014, which is a continuation of application Ser. No. 13/743,824, filed Jan. 17, 2013, which is a continuation of application Ser. No. 12/806,941, filed Aug. 24, 2010, which is a continuation of application Ser. No. 11/355,737, filed Feb. 16, 2006, abandoned, which claims the priority of provisional Application Ser. No. 60/654,567, filed Feb. 18, 2005, the disclosures of which are incorporated by reference in their entireties.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Not Applicable

BRIEF SUMMARY OF THE INVENTION

Not Applicable

DETAILED DESCRIPTION OF THE INVENTION

This application relates to polyphosphazene polymers having immunomodulating activity and the biomedical use of such polyphosphazene polymers in conjunction with an antigen or an immunogen.

A wide variety of antigens stimulate the production of antibodies in animals thereby conferring protection against infection. However, some antigens are unable to stimulate an effective immune response treatment.

The immunogenicity of a relatively weak antigen is often enhanced by the simultaneous administration of the antigen with an adjuvant, a substance that is not immunogenic when administered alone, but which will induce a state of systemic, humoral, and/or mucosal immunity when combined with the antigen. It has been traditionally thought that adjuvants, such as mineral oil emulsions or aluminum hydroxide, form an antigen depot at the site of injection that slowly releases antigen. Unfortunately, many immunoadjuvants, such as Freund's Complete Adjuvant, are toxic and are therefore only useful for animal research purpose, not human vaccinations. Freund's Complete Adjuvant contains a suspension of heat-killed *Mycobacterium tuberculosis* in mineral oil containing a surfactant, and it causes granulomatous lesions in animals at the site of immunization. Freund's adjuvant may also cause the recipient of a vaccine to test positive for tuberculosis.

Some synthetic polymers have been found to provide immunostimulation when combined with an antigen. For example, the adjuvant activities of polyacrylic acid (PAA), copolymers of acrylic acid and N-vinylpyrrolidone (CP-AAVPD), poly-2-methyl-5-vinyl pyridine (PMVP), poly-4-vinylN-ethylpyridinium bromide (PVP-$R_2$) and similar compounds, when conjugated to an antigen, have been studied (V. A. Kabanov, *From Synthetic Polyelectrolytes to Polymer—Subunit Vaccines*, Pure Appl. Chem., 2004, 76, 9, 1659-1677). However, these polymers require covalent attachment of antigen to the polymer in order to elicit effective immune responses, which can present manufacturing and regulatory challenges. In addition, toxicity and biodegradability of the majority of these polymers have not been studied and may prevent use of these polymers as adjuvants for applications in humans.

Poly[di(carboxylatophenoxy)phosphazene] (PCPP), polyphosphazene polymer is described as an immunoadjuvant that does not require covalent attachment of antigen to the polymer in order to elicit effective immune responses (L. G. Payne, S. A. Jenkins, A. L. Woods, E. M. Grund, W. E. Geribo, J. R. Loebelenz, A. K. Andrianov, B. E. Roberts, *Poly[di(carboxylatophenoxy)phosphazene] (PCPP) is a potent immunoadjuvant for an influenza vaccine*; Vaccine 16, 92-98 (1998)). However, more potent immunoadjuvants than PCPP are needed.

A non-toxic adjuvant or carrier having the ability to stimulate an immune response to non-antigenic or weakly antigenic molecules would fill a long-sought need in the development and administration of vaccines.

The present invention provides polyphosphazenes that may be used as adjuvants and are superior in their immunoadjuvant activity to PCPP.

Polyphosphazenes are polymers with backbones including alternating phosphorus and nitrogen atoms, separated by alternating single and double bonds. Each phosphorous atom is covalently bonded to two pendant groups ("A").

The repeat unit of a polyphosphazene has the following formula:

wherein each "A" may be the same, or different, and wherein the unit is repeated "n" times.

When the polyphosphazene has only one type of pendant group or side group repeatedly attached to its backbone the polymer is said to be a homopolymer. When the polyphosphazene has more than one type of pendant group and the groups vary randomly throughout the polymer, the polyphosphazene is a random copolymer. Phosphorous can be bound to two like groups, or to two different groups.

Polyphosphazenes can be produced by reacting macromolecular precursor—poly(dichlorophosphazene) with the desired nucleophiles, such as alcohols, amines, or thiols. Polyphosphazenes with two or more types of pendant groups can be produced by reacting poly(dichlorophosphazene) with two or more types of nucleophiles in a desired ratio. Nucleophiles can be added to the reaction mixture simultaneously or in sequential order. The resulting ratio of pendant groups in the polyphosphazene will be determined by a number of factors, including the ratio of starting materials used to produce the polymer, the order of addition, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

The polymers of the present invention may be produced by initially producing a reactive macromolecular precursor—poly(dichlorophosphazene). The pendant groups are then substituted onto the polymer backbone by reaction between the reactive chlorine atoms on the backbone and the appropriate organic compound. For example, an organic compound containing hydroxyl group and ester group may be reacted with the reactive chlorine atoms on the polymer backbone. One or a mixture of organic compounds can be used to result in a homopolymer or mixed substituent copolymers correspondingly. Hydroxyl group of the organic compound can be activated with sodium, sodium hydride, or sodium hydroxide by procedures known in the art and then reacted with chlorine atoms attached to the polyphosphazene backbone. After the completion of the reaction, the ester functionalities of the pendant groups may be hydrolyzed to yield carboxylic acid functionalities. All ester functionalities can be hydrolyzed to achieve full conversion into the acid groups, or, if desired, the reaction can be stopped before the completion resulting in a mixed substituted copolymer containing both acid and ester functionalities. Polymer then can be dissolved in aqueous solutions at the desired concentration. Acid groups can be also converted into salt form, such as sodium or potassium, if required to improve solubility or to achieve desired polymer conformation and physicochemical characteristics.

Thus, in one aspect, the present invention provides a polyphosphazene polymer that contains repeating units of the following formula:

wherein in each monomeric unit of the polymer, each R is the same or different, and wherein in at least a portion of the monomeric units of the polymer one or more of the R groups is "W." Wherein "W" is:

-continued wherein: $X = -\!\!-\!\!(O-CH_2)_d\!\!-\!\!;\ -\!\!-\!\!NH-\!\!(CH_2)_d\!\!-\!\!;$ or
$-\!\!-\!\!S-\!\!(CH_2)_d\!\!-\!\!;$ $Y = -\!\!-\!\!(O-CH_2)_e\!\!-\!\!H;$ $Y' = -\!\!-\!\!(O-CH_2)_{e'}\!\!-\!\!H;$ $C = -\!\!-\!\!(CH_2)_f\!\!-\!\!COOH;\ \phantom{xx}$ ⟨C₆H₄⟩—COOH; or $-\!\!-\!\!(O-CH_2)_g\!\!-\!\!H;$ $C' = -\!\!-\!\!(CH_2)_f\!\!-\!\!COOH;\ \phantom{xx}$ ⟨C₆H₄⟩—COOH; or $-\!\!-\!\!(O-CH_2)_{g'}\!\!-\!\!H;$ $C'' = -\!\!-\!\!(CH_2)_f\!\!-\!\!COOH;\ \phantom{xx}$ ⟨C₆H₄⟩—COOH; or $-\!\!-\!\!(O-CH_2)_{g''}\!\!-\!\!H;$ wherein at least one of C, C', or C" includes —COOH; each of d, f, f', are from 0 to 3; and
each of e, e', g, g', g" are from 0 to 1;
and if
f=0, such that
C=—COOH
then at least one of C', C", Y, or Y' is other than hydrogen; or X is other than —O—, —NH—, or —S—;
and the sum of d+e+e'++f'+g'+g" equals from 1 to 8.
The carboxylic acid groups can be either in ionized or non-ionized form.

It is an aspect of the instant invention that the polyphosphazene polymer as hereinabove described and as hereinbelow described has an overall molecular weight of 5,000 g./mol. to 10,000,000 g./mol. It is a further aspect of the instant invention that the polyphosphazene polymer contains a minimum number of monomer units having the hereinabove-described and hereinbelow-described immunostimulating carboxylic acid containing groups. While it is within the ordinary skill that prevails in the art when considered in conjunction with the instant disclosure to determine how many of the hereinabove-described and hereinbelow-described monomeric units will result in an immunostimulating polyphosphazene polymer, it is an aspect of the instant invention that the polyphosphazene polymer contains at least 10 of the above-described carboxylic acid containing monomeric units.

The remaining R groups (those other than the immunostimulating carboxylic acid containing groups as described above) may be one or more of a wide variety of substituent groups. As representative, non-limiting examples of such groups there may be mentioned: aliphatic; aryl; aralkyl; alkaryl; carboxylic acid; heteroaromatic; carbohydrates, including glucose; heteroalkyl; halogen; (aliphatic)amino— including alkylamino-; heteroaralkyl; di(aliphatic)amino— including dialkylamino-, arylamino-, diarylamino-, alkylarylamino-; -oxyaryl including but not limited to -oxyphenylCO$_2$H, -oxyphenylSO$_3$H, -oxyphenylhydroxyl and -oxyphenylPO$_3$H; -oxyaliphatic including -oxyalkyl, -oxy(aliphatic)CO$_2$H, -oxy(aliphatic)SO$_3$H, -oxy(aliphatic) PO$_3$H, and -oxy(aliphatic)hydroxyl, including oxy(alkyl) hydroxyl; -oxyalkaryl, -oxyaralkyl; -thioaryl; thioaliphatic including -thioalkyl; -thioalkaryl; thioaralkyl; —NHC(O)O-(aryl or aliphatic); —O—[(CH$_2$)xO]y-CH$_2$)—O—[(CH$_2$)

xO]y(CH₂)xNH(CH₂)xSO₃H; and —O—[(CH₂)xO]y-(aryl or aliphatic); wherein x is 1-8 and y is an integer of 1 to 20. The groups can be bonded to the phosphorous atom through, for example, an oxygen, sulfur, nitrogen, or carbon atom.

In yet another aspect, the present invention provides a polyphosphazene polymer that contains repeating units of the following formula:

wherein in each monomeric unit of said polymer, each R is the same or different, and wherein in at least a portion of the monomeric units of the polymer one or more of the R groups is:

wherein and wherein d is from 0 to 15.

It is an aspect of the instant invention that the polyphosphazene polymer as hereinabove described and as hereinbelow described has an overall molecular weight of 5,000 g./mol. to 10,000,000 g./mol. It is a further aspect of the instant invention that the polyphosphazene polymer contains a minimum number of monomer units having the hereinabove-described and hereinbelow-described immunostimulating carboxylic acid containing groups. While it is within the ordinary skill that prevails in the art when considered in conjunction with the instant disclosure to determine how many of the hereinabove-described and hereinbelow-described monomeric units will result in an immunostimulating polyphosphazene polymer, it is an aspect of the instant invention that the polyphosphazene polymer contains at least 10 of the above-described carboxylic acid containing monomeric units.

The remaining R groups (those other than the immunostimulating carboxylic acid containing groups as described above) may be one or more of a wide variety of substituent groups. As representative, non-limiting examples of such groups there may be mentioned: aliphatic; aryl; aralkyl; alkaryl; carboxylic acid; heteroaromatic; carbohydrates, including glucose; heteroalkyl; halogen; (aliphatic)amino— including alkylamino-; heteroaralkyl; di(aliphatic)amino— including dialkylamino-, arylamino-, diarylamino-, alkylarylamino-; -oxyaryl including but not limited to -oxyphenylCO₂H, -oxyphenylSO₃H, -oxyphenylhydroxyl and -oxyphenylPO₃H; -oxyaliphatic including -oxyalkyl, -oxy(aliphatic)CO₂H, -oxy(aliphatic)SO₃H, -oxy(aliphatic)PO₃H, and -oxy(aliphatic)hydroxyl, including oxy(alkyl)hydroxyl; -oxyalkaryl, -oxyaralkyl; -thioaryl; thioaliphatic including -thioalkyl; -thioalkaryl; thioaralkyl; —NHC(O)O-(aryl or aliphatic); —O—[(CH₂)xO]ᵧ—CH₂)—O—[(CH₂) xO]y(CH₂)xNH(CH₂)xSO₃H; and —O—[(CH₂)xO]y-(aryl or aliphatic); wherein x is 1-8 and y is an integer of 1 to 20. The groups can be bonded to the phosphorous atom through, for example, an oxygen, sulfur, nitrogen, or carbon atom.

Figure 1:
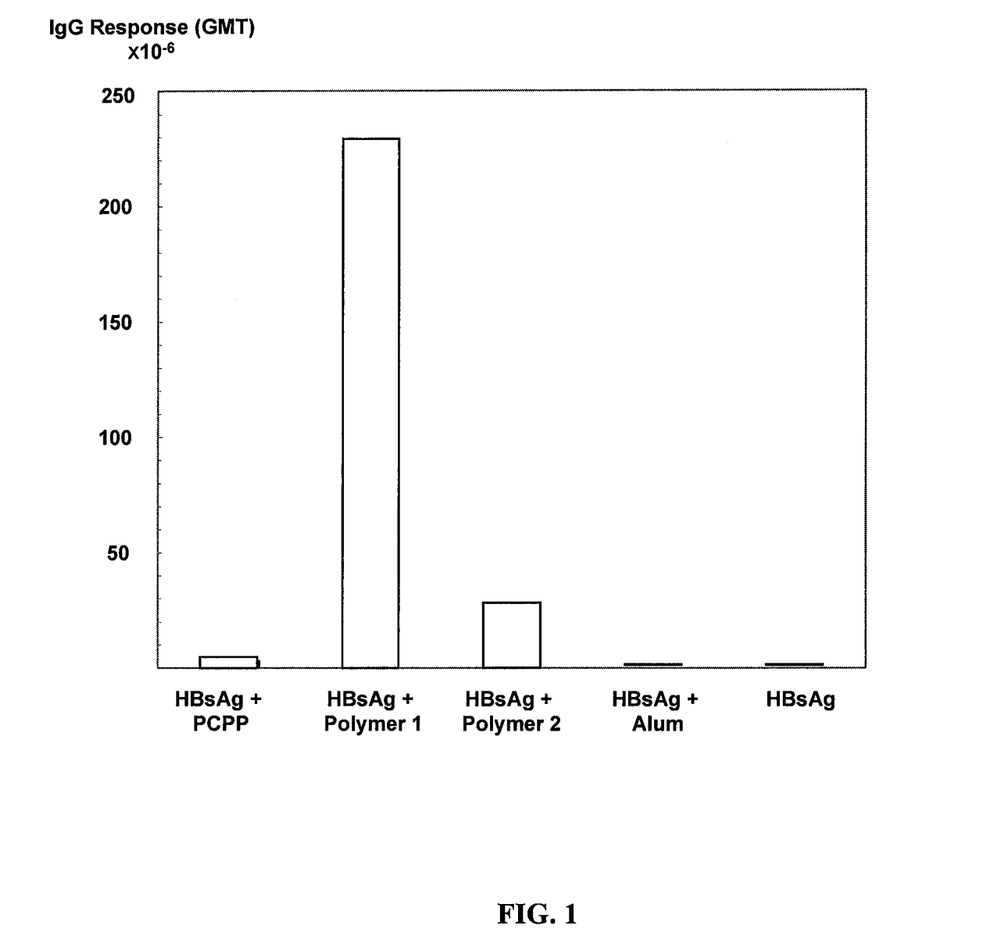
FIG. 1 represents serum IgG titers after immunization of mice with HBsAg formulated with Polymer 1 and Polymer 2. HBsAg, HBsAg formulated with PCPP, and HBsAg formulated with Alum were used as controls (5 BALB/c mice per group; HBsAg: 1 µg/mouse; polymers: 50 µg/mouse; single dose intramuscular injection; 16 week data).

Two examples of polyphosphazenes that are particularly preferred as immunoadjuvants are:

Both of these compounds exhibited significantly better adjuvant activity in comparison to poly[di(carboxylatophenoxy) phosphazene] (PCPP), as is shown in FIG. 1

Preferred polyphosphazenes of the present invention have a molecular weight of at least 5,000 g/mol while generally not exceeding 10,000,000 g/mol.

Polyphosphazenes of present invention can be homopolymers, having one type of side groups, or mixed substituent copolymers, having two or more types of side groups. In mixed substituent copolymers there is at least one type of side group that contains carboxylic acid functionality and one type of side groups that does not contain carboxylic acid functionality. Side groups that do not contain carboxylic acid functionalities can be introduced in a polyphosphazene copolymer to modulate physical or physico-chemical properties of the polymer. Such side groups can be used, for example, to improve water-solubility, to modulate biodegradability, to increase hydrophobicity, or to change chain flexibility of the polymer. As non-limiting examples of such non-carboxylic acid functionality containing physical or physico-chemical property modulating side groups there may be mentioned phenoxy, alkoxy, hydroxy, halogen, and methoxyethoxyethoxy. Examples of copolymers that are particularly preferred as immunoadjuvants are polymer that contain monomeric units such as the following:

Wherein a is between 0.1 and 1.9, b is between 1.9 and 0.1, and a +b=2.

The polyphosphazenes of the present invention are polymers that are preferably biodegradable when administered to either humans or animals. Biodegradability of the polymer prevents eventual deposition and accumulation of polymer molecules at distant sites in the body, such as the spleen. The term biodegradable, as used herein, means a polymer that degrades within a period that is acceptable in the desired application, typically less than about five years and most preferably less than about one year.

Polyphosphazenes for use as immunoadjuvants can be cross-linked. Ionically-crosslinked polyphosphazenes, for example, can be prepared by combining a phosphazene polymer with a multivalent metal cation such as zinc, calcium, bismuth, barium, magnesium, aluminum, copper, cobalt, nickel, cadmium, or other multivalent metal cation known in the art; or with a multivalent organic cation such as spermine, spermidine, poly(ethyleneimine), poly(vinylamine), or other multivalent organic cation known in the art.

Polymers of the present invention can be used in combination with an antigen; the antigen may be any one of a wide variety of antigens against which an immune response is desired. The polymer upon mixing with the antigen can form non-covalent complexes. Such complexes can be water-soluble or in the form of microgels or other microparticulates, including microspheres. Complexes can contain single polyphosphazene molecules and multiple antigen molecules or single antigen molecules and multiple polyphosphazene molecules. Alternatively, complexes can contain multiple molecules of both polyphosphazenes and antigens. Such complexes have the ability to present the antigen to the corresponding immune competent cell or to release antigen over an extended period of time. The immunogenic response may be humoral, mucosal, and/or cell mediated.

The polymer in combination with an antigen is used in an amount effective to provide the desired immune response. The immunogenic composition can be administered as a vaccine by any method known to those skilled in the art that elicits an immune response; including parenteral, oral, or transmembrane or transmucosal administration. Preferably, the vaccine is administered parenterally (intravenously, intramuscularly, subcutaneously). Non-limiting examples of routes of delivery to mucosal surfaces are intranasal (or generally, the nasal associated lymphoid tissue), oral, respiratory, vaginal and rectal.

An immunogenic composition is prepared by either mixing or conjugating the polymer adjuvant with an antigen prior to administration. Alternatively, the polymer and antigen can be administered separately to the same site.

The polymeric adjuvant of the invention is a polyphosphazene that is preferably soluble in water at physiological pH, i.e., preferably has a solubility of at least 0.0001% (w/w).

The antigen with which the adjuvants of the invention are used can be derived from a cell, a bacteria or virus particle or a portion thereof. The antigen can be a protein, peptide, polysaccharide, glycoprotein, glycolipid, or combination thereof which elicits an immunogenic response in a human; or in an animal, for example, a mammal, bird, or fish. The immunogenic response can be humoral, mucosal, or cell mediated. Where the material against which an immune response is directed is poorly antigenic, such material may be conjugated to a carrier such as albumin, or to a hapten, using standard covalent binding techniques. Such conjugation can be effected with commercially available reagent kits that are well known in the art.

In one embodiment, the polymer is used to deliver nucleic acid, which encodes antigen to a mucosal surface where the nucleic acid is expressed.

As non-limiting examples of antigens that may be contained in the polyphosphazene complexes, hydrogels, micropraticles, or microspheres there may be mentioned viral proteins, such as influenza proteins, human immunodeficiency virus (HIV) proteins, Herpes virus proteins, and hepatitus A and B proteins. Additional examples include antigens derived from rotavirus, measles, mumps, rubella, and polio; or from bacterial proteins and lipopolysaccharides such as Gram-negative bacterial cell walls. Further antigens may also be those derived from organisms such as *Haemophilus influenza, Clostridium tetani, Corynebacterium diphtheria*, and *Nesisseria gonhorrhoae*.

An immunogenic composition, or vaccine, is prepared by combining the polymer adjuvant with an antigen. Approximately 0.0001-5 parts of antigen is added to one part of polymer, preferably by stirring a solution of polymer and antigen until a solution or suspension is obtained, preferably for 10 minutes or more at about 25° C. The polymer is preferably combined with the antigen using a method dispersing the antigen uniformly throughout the adjuvant. Methods for liquefying the polymer include dissolving the polymer in an aqueous-based solvent, preferably having a pH range of between 7.1 and 7.7; or melting the polymer. The latter is useful only when the antigen is stable at the polymer melting temperature. The antigen is then mixed with the polymer. The polymer and the antigen, in solid form, for example, when the antigen is lyophilized, can also be physically mixed together, for example, by compression molding. The polymer can also be used to encapsulate the antigen, for example, using the methods of U.S. Pat. No. 5,149,543 issued to Cohen et al.; or U.S. Pat. No. 5,807,757 issued to Andrianov et al., the teachings of which are hereby incorporated by these references thereto, or by spray drying a solution of polymer and antigen. Alternatively, microspheres containing the antigen and adjuvant can be prepared by simply mixing the components in an aqueous solution, and then coagulating the polymer together with the substance by mechanical forces to form a microparticle, as is described in U.S. Pat. No. 5,500,161 issued to Andrianov et al. The microparticle can be stabilized, if necessary or desired, using electrolytes, pH changes, organic solvents, heat, or frost to form polymer matrices encapsulating biological material.

The preferred polymers of the present invention are soluble in physiologically buffered saline (PBS, pH 7.4).

It will be understood by those skilled in the art that the immunogenic vaccine composition can contain other physiologically acceptable ingredients such as water; saline; and or surfactants. The polymer can be combined with other adjuvants.

The polymer of present invention can be combined with an amphiphilic compound. The amphiphilic compound may or may not function as an adjuvant in the absence of the water soluble polymer.

The term amphiphilic compound as known in the art means that the compound includes both a hydrophobic portion and a hydrophilic portion. As non-limiting examples of the amphiphilic compounds suitable for producing the adjuvant of the present invention there may be mentioned dimyristoyl phosphatidylcholine, dimethyldioctadecylammonium bromide, N,N-dioctadecyl-N',N'-bis(2-hydroxyethyl)propanediamine, N-(2-Deoxy-2-L-leucylamino-β-D-glucopyranosyl)-N-octadecydodecanoylamide hydroacetate, dimyristoyl phosphatidylglycerol, N-acetylglucosaminyl-N-acetylmuramyl-L-Ala-D-isoGlu-L-Ala-glycerol dipalmitate, sorbitan trioleate, deoxycholic acid sodium salt, dicetyl phosphate, mono-palmitoyl-rac-glycerol, N-acetylglucosaminyl-N-acetylmuramyl-L-Ala-D-iso-Glu-L-Ala-dipalrnitoxy propylamide, octadecyl tyrosine hydrochloride, D-murapalmitine, 3-O-desacyl-4'-monophosphoryl lipid A, mannide oleate, 1a,25-dihydroxyvitamin $D_3$, phosphatidic acid, phosphatidylethanolamine, phosphatidylcholine, phosphatidylserine, phosphatidylinositol, sphingo sine (D-4-sphingenine, ceramides, sphingomyelin, galactosylceramide, $GM_2$ (ganglioside), salts of fatty acids including oleic acid, palmitic acid, capric acid, lauric acid, myristic acid, stearic acid, arachidic acid, behenic acid, lignoceric acid, cerotic acid, linoleic acid, linolenic acid, arachidonic acid, and the like.

In one aspect, the adjuvant can be prepared by mixing the water soluble polymer and the amphiphilic compound at room temperature. Antigen is then added to the adjuvant combination. Alternatively, the antigen is first mixed with one of the adjuvant components, and then the second adjuvant component is added. Preferably the immunogenic composition of the present invention is prepared by either mixing or conjugating the water soluble polymer with the antigen prior to administration. The water soluble polymer/antigen combination is then combined with the amphiphilic compound to form the immunogenic composition.

In one aspect of the present invention the polyphosphazenes may be used to comprise vaccines, which vaccines may be directed to the treatment, or prevention, of disease.

The dosage is determined by the antigen loading and by standard techniques for determining dosage and schedules for administration for each antigen, based on titer of antibody elicited by the polymer-antigen administration, as demonstrated by the following examples.

Although in the preferred embodiment the polymer antigen mixture is administered simultaneously, in an alternative embodiment, the polymer and antigen are administered separately to the same or nearby site.

The polyphosphazene adjuvants and methods of synthesis will be further understood by reference to the following non-limiting examples.

Example 1

Synthesis of poly{di[4-(2-carboxyethyl)phenoxy]phosphazene}. In a nitrogen atmosphere, methyl 3-(4-hydroxyphenyl)propionic acid (25.0 g; 0.139 moles) was dissolved in diethylene glycol dimethyl ether, diglyme (0.45 L). 1.55 g of 65% sodium hydride (0.042 moles) was added to the mixture over a ten minute period. To the resulting mixture polydichlorophosphazene (1.25 g; 0.011 moles) was slowly added via syringe under nitrogen atmosphere at 110° C. while stirring. The reaction was stirred for three hours at 110° C. and then cooled to 85° C. To this mixture 0.1 L of 12.7 N potassium hydroxide was added. The reaction was stirred for one hour at 85° C., and then was cooled to ambient temperature.

The reaction mixture was transferred into a large separating funnel. The polymer-containing aqueous layer was removed and collected. 0.5 L of deionized water was added to the organic layer, shaken, and the aqueous phase was separated and collected. The procedure was repeated two times. Aqueous solution was then acidified with 4 N hydrochloric acid to pH 2. The precipitate was collected and then dissolved in 0.4 L of 0.5 N potassium hydroxide. Upon dissolution, the pH was adjusted by the addition of hydrochloric acid to pH 9-10.5. The polymer was then purified by size-exclusion chromatography using a Biocad workstation. Polymer fractions were collected and then precipitated by the addition of 0.5 N hydrochloric acid until pH of 2 was reached. The precipitate was filtered, washed with water until the rinse became neutral, and dried in vacuum. The yield was 3 g.

Examples 2-12

Polymers were synthesized as described in Example 1. Polymer structures, reagents, reagent quantities, and reaction conditions are shown in Table 1.

TABLE 1

Polymer structures, reagents, and reaction conditions for examples 2-12.

| Ex. No | Polymer Structure | Reagent(s) Name | Amount, g (mmol) | NaH,* G (mmol) | PDCP, g (meq) | T ° C. | Molecular Weight ×10⁻³, g/mol |
|---|---|---|---|---|---|---|---|
| 1 | [structure: phosphazene with two -O-C₆H₄-CH₂-CH₂-COOH groups, -(P=N)ₙ-] | Methyl 3-(4-hydroxyphenyl) propionate | 25 (139) | 1.55 (42) | 1.25 (21.6) | 110 | 200 |

TABLE 1-continued

Polymer structures, reagents, and reaction conditions for examples 2-12.

| Ex. No | Polymer Structure | Reagent(s) Name | Amount, g (mmol) | NaH,* G (mmol) | PDCP, g (meq) | T °C. | Molecular Weight ×10⁻³, g/mol |
|---|---|---|---|---|---|---|---|
| 2 | [structure] | 4-hydroxybenzoic acid methyl ester | 4.21 (25.36) | 0.47 (12.68) | 0.150 (2.58) | 120 | 300 |
| 3 | [structure] | Methyl 4-hydroxy phenylacetate | 1.33 (8.00) | 0.15 (4.00) | 0.116 (2.00) | 120 | 990 |
| 4 | [structure] | Ethyl 4'-hydroxy-4-biphenylcarboxylate | 4.41 (18.19) | 0.34 (9.09) | 0.210 (3.62) | 90 | 340 |
| 5 | [structure] | Ethyl homovanillate | 1.68 (7.97) | 0.15 (3.98) | 0.210 (3.62) | 90 | 340 |
| 6 | [structure] | Methyl vanillate | 3.31 (18.19) | 0.34 (9.09) | 0.210 (3.62) | 90 | 1100 |

TABLE 1-continued

Polymer structures, reagents, and reaction conditions for examples 2-12.

| Ex. No | Polymer Structure | Reagent(s) Name | Amount, g (mmol) | NaH,* G (mmol) | PDCP, g (meq) | T °C. | Molecular Weight ×10$^{-3}$, g/mol |
|---|---|---|---|---|---|---|---|
| 7 | [(O—C$_6$H$_4$—CH$_2$—COOH)$_a$ / P=N / (O—C$_{10}$H$_{20}$—H)$_b$]$_n$ | Methyl 4-hydroxy Phenylacetate (90%) | 2.72 (16.37) | 0.30 (8.18) | 0.210 (3.62) | 90 | 510 |
|  |  | 1-Decanol (10%) | 0.29 (1.82) | 0.03 (0.91) |  |  |  |
| 8 | [(O—C$_6$H$_4$—CH$_2$—CH$_2$—COOH)$_a$ / P=N / (O—C$_6$H$_5$)$_b$]$_n$ | Methyl 3-(4 Hydroxyphenyl) Propionate (90%) | 1.1 (6.08) | 0.15 (4.05) | 0.087 (1.5) | 120 | 600 |
|  |  | Phenol (10%) | 0.064 (0.675) | 0.017 (0.45) |  |  |  |
| 9 | O—CH(CH$_3$)—COOH / (P=N)$_n$ / O—CH(CH$_3$)—COOH | Ethyl lactate | 4.30 (36.38) | 0.34 (9.09) | 0.210 (3.62) | 90 | 10 |
| 10 | O—CH$_2$—C(CH$_3$)$_2$—COOH / (P=N)$_n$ / O—CH$_2$—C(CH$_3$)$_2$—COOH | Methyl 2,2-dimethyl-3-hydroxypropionate | 1.60 (12.13) | 0.11 (3.03) | 0.140 (2.41) | 120 | 50 |
| 11 | O—(CH$_2$)$_6$—COOH / (P=N)$_n$ / O—(CH$_2$)$_6$—COOH | Ethyl 6-hydroxyhexanoate | 5.08 (31.69) | 0.59 (15.85) | 0.132 (2.28) | 130 | 230 |
| 12 | O—C$_6$H$_{10}$—COOH / (P=N)$_n$ / O—C$_6$H$_{10}$—COOH | Ethyl 4-hydroxycyclohexanecarboxylate | 2.18 (12.68) | 0.23 (6.34) | 0.075 (1.30) | 120 | 60 |

*65% suspension of sodium hydride in oil was used. The amounts are shown for a suspension (in g) and for sodium hydride (in mmole).

Example 13

Polymers synthesized as described in examples 1 (Polymer 1) and example 2 (Polymer 2) were evaluated in vivo for their ability to enhance the immune response (adjuvant activity) to Hepatitis B surface antigen—HBsAg (Biodesign International). BALB/c mice were used (5 mice per group). 1 μg of HBsAg mixed with 50 μg of the polymer in solution (final volume 100 μl) was injected in each mouse. Formulations containing antigen alone, antigen formulated with 50 μg of PCPP, and antigen formulated with Alum were used as controls. Mice were immunized with a single intramuscular injection. Blood samples were collected 16 weeks post-immunization and serum stored until analysis.

Antigen-specific antibodies (IgG) in mouse serum were determined by ELISA in 96-well Immunolon II plates coated with HBsAg in sodium carbonate buffer, pH 9.6. The plates were washed six times with PBS containing 0.05% Tween 20 (PBST). Two-fold serial dilutions of sera in PBST containing 0.5% gelatin were added to the wells and the plate was incubated 2 hours at ambient temperature. Unbound serum was removed by washing the plates six times with PBST. Biotinylated Goat Anti-Mouse IgG (Caltag Laboratories) was added and the plates were incubated for 1 hour at ambient temperature. The plates were washed six times with PBST and alkaline phosphatase conjugated. Streptavidin (BioCan Scientific) was added and plates were incubated for 1 hour at ambient temperature. Unbound conjugate was removed by washing eight times with deionized water and serum antibodies were detected by adding 1 mg/mL of p-nitrophenyl phosphate di(Tris) salt in 1% Diethanolamine—0.5 mM magnesium chloride buffer, pH 9.8. The reaction was allowed to run for 15 minutes and the absorbance was measured at 405 nm using Benchmark™ Microplate Reader (Bio-Rad Laboratories, Hercules, Calif.). The endpoint titers were the reciprocal of the highest sample dilution producing a signal identical to that of an antibody-negative sample at the same dilution plus three times standard deviation. The average antibody titers for a group of mice were expressed as geometric mean titers (GMT).

The results are presented in FIG. 1. Both Polymer 1 and Polymer 2 showed significantly higher adjuvant activity than PCPP and alum.

Example 14

Figure 2:
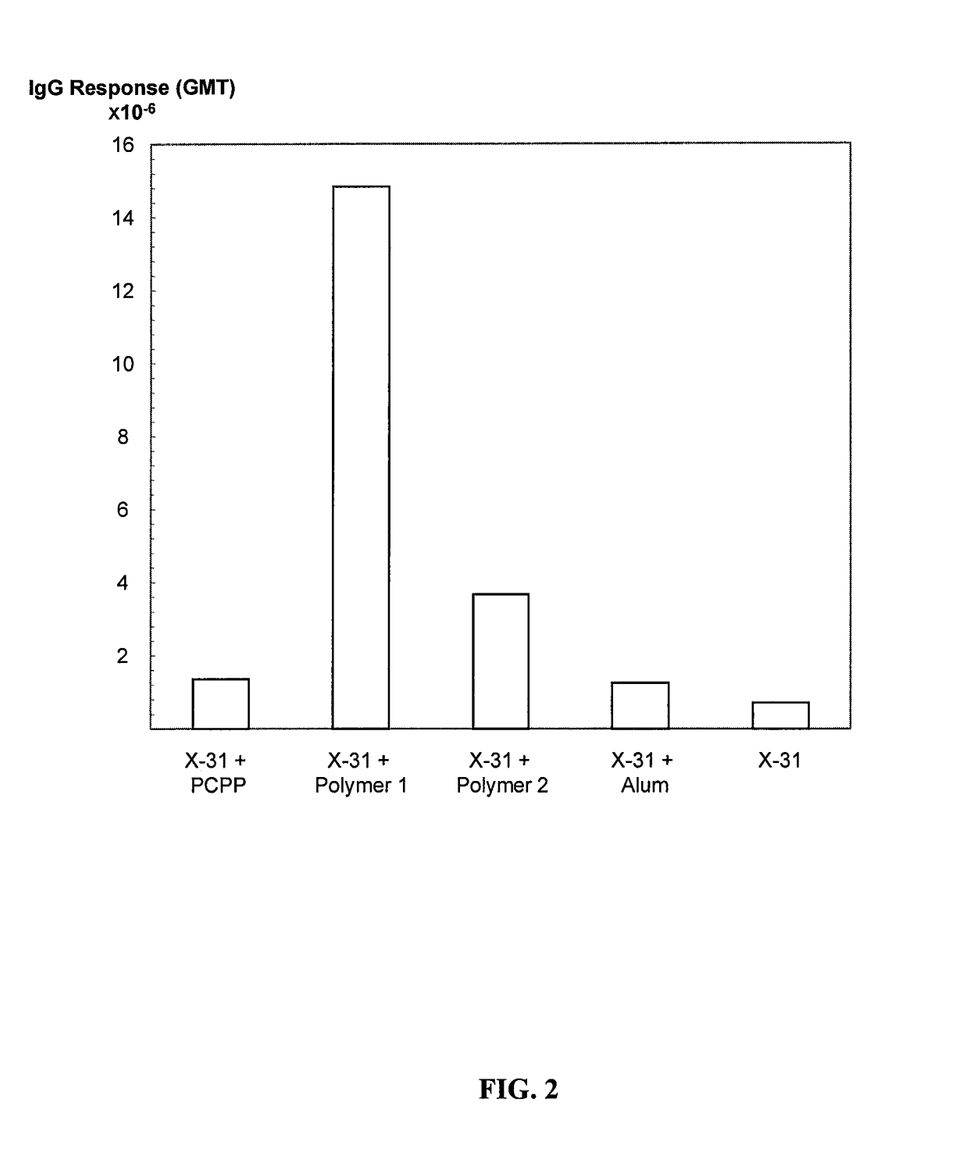
FIG. 2 represents serum IgG titers after immunization of mice with X-31 influenza formulated with Polymer 1 and Polymer 2. X-31, X-31 formulated with PCPP, and X-31 formulated with Alum were used as controls (5 BALB/c mice per group; X-31: 5 µg/mouse; polymers: 50 µg/mouse; single dose intramuscular injection; 16 week data).

Polymers 1 and 0.2 were evaluated in mice similarly as described in Example 13, except that 5 μg X-31 influenza (Charles River Laboratories) was used instead of HBsAg. The results are presented in FIG. 2. Both Polymer 1 and Polymer 2 showed significantly higher adjuvant activity than PCPP and alum.

What is claimed is:
1. A composition for inducing an immunogenic response in a human or in an animal comprising an antigen and a homopolymer having the following structural formula:

wherein said homopolymer has a molecular weight of 5,000 g/mol. to 10,000,000 g/mol.

* * * * *